United States Patent [19]

Bentall et al.

[11] Patent Number: 4,611,599

[45] Date of Patent: Sep. 16, 1986

[54] ELECTRICAL APPARATUS FOR INFLUENCING THE METABOLIC CHARACTERISTICS OF LIVING SYSTEMS

[75] Inventors: Richard H. C. Bentall, The Basement, 7 Penzance Place, London, W11 4PE, England; Timothy J. Cox, Midlothia; Ronald D. L. Mackie, Edinburgh, both of Scotland

[73] Assignee: Richard Hugh Cameron Bentall, London, England

[21] Appl. No.: 621,049

[22] Filed: Jun. 15, 1984

[30] Foreign Application Priority Data

Jun. 16, 1983 [GB] United Kingdom ............... 8316377

[51] Int. Cl.⁴ .............................................. A61N 1/42
[52] U.S. Cl. ................................................. 128/422
[58] Field of Search ............... 128/419 R, 421, 422, 128/423 R, 804, 419 PS

[56] References Cited

U.S. PATENT DOCUMENTS

| | | | |
|---|---|---|---|
| 2,099,511 | 11/1937 | Caesar | 128/423 R |
| 3,566,877 | 3/1971 | Smith et al. | 128/804 |
| 3,942,535 | 3/1976 | Schulman | 128/419 PS |
| 4,249,537 | 2/1981 | Lee et al. | 128/422 |

Primary Examiner—William E. Kamm
Attorney, Agent, or Firm—Steele, Gould & Fried

[57] ABSTRACT

An electrical apparatus applies an electric field, e.g. a r.f. field, in a timed manner such that over a given cycle period, e.g. 24 hours, the field is applied for a selected portion of the cycle period and is switched off for the remainder of the period. The periods may be programmable utilizing a microprocessor. The field strength may be selected so as not to produce significant tissue heating, typically less than approximately 100 $\mu w/cm^2$, measured at a system surface.

12 Claims, 5 Drawing Figures

ELECTRICAL APPARATUS FOR INFLUENCING THE METABOLIC CHARACTERISTICS OF LIVING SYSTEMS

BACKGROUND OF THE INVENTION

This invention relates to electrical apparatus for influencing the metabolic characteristics of living systems and has particular but not exclusive application to apparatus for applying a high frequency electromagnetic field to living tissue to promote healing thereof, at a sufficiently low field strength as not to produce any substantial tissue heating.

It has been known for many years that improved healing rates can be achieved by applying r.f. (radio frequency) electromagnetic fields to wounded tissue in such a manner as to produce tissue heating. This heating technique is known as diathermy.

More recently it has been appreciated that the therapy produced by an applied r.f. field is not characterised solely in terms of the tissue heating effect of the field. A discussion of this subject is given in "Healing by Electromagnetism - Fact or Fiction" New Scientist Apr. 22, 1976.

In published U.K. Patent Application No. 2027594 and corresponding U.S. Pat. No. 4,412,540 (Dr.R.H.C. Bentall) there is described a portable low power apparatus for attachment to a patient to produce therapy with an electromagnetic field which does not produce any substantial tissue heating. The portable apparatus comprises a battery driven r.f. oscillator and an antenna which is flexible to overlie an area of tissue to be treated. The apparatus thus can be attached to the patient and is left running on a continuous basis for the entire period for which it is desired to effect therapy. The portable apparatus produces an electromagnetic field typically in the frequency range 3-30 MHz, the particular r.f. frequency not being of great significance as to the efficacy of the treatment. The r.f. field is pulsed to maximise the therapeutic effect, typically so as to produce r.f. pulses 100 $\mu$sec duration at intervals of 1 $\mu$sec. The portable device operates at power levels typically of less than 100 $\mu$W cm$^{-2}$ as measured at the skin of the tissue, and thus at a level which does not produce any substantial tissue heating.

SUMMARY OF THE INVENTION

In accordance with the present invention it has been appreciated that an apparatus producing a field for influencing a living system, does not have to produce the field (pulsed or otherwise) on a continuous basis, but that satisfactory results may be achieved if the field is applied for a period for example, for a period of several hours and is then switched off or reduced for several hours before being switched on again.

More particularly, in accordance with the present invention it has been appreciated that, for an electromagnetic field which does not produce any substantial tissue heating, effective therapy can be performed by applying the electromagnetic field to the tissue intermittently during the desired period of therapy rather than on a continuous basis for the entire therapy period.

Broadly, in accordance with the invention there is provided electrical apparatus for influencing the metabolic characteristics of living systems, comprising means for applying an electric field to a living system to alter a metabolic characteristic thereof, the electric field having a predetermined characteristic, and timing means for causing said field applying means to apply said field with said characteristic, repetitively for periods spaced apart in time.

More particularly, in accordance with the present invention there is provided an electrical therapy apparatus comprising means for applying a r.f. electromagnetic field to living tissue to promote healing thereof (that is, tissue growth) but without producing any significant tissue heating, and timing means for causing said field applying means to operate intermittently. The r.f. field may itself be pulsed, for example to produce pulses 100 $\mu$sec wide at intervals of 1 $\mu$sec, and the operative periods of the field applying means defined by the timing means are significantly longer than such pulse periods, for example several hours.

The timing means may be adapted to define a sequence of cycle periods, for example each of 24 hours, and to render the field applying means operative for a predetermined portion of each cycle period. Thus, for example, the field may be produced for eight hours within each 24 hour period. Preferably, means are provided to select the duration of said predetermined portion of the cycle period.

Therapy may be performed for a plurality of successive cycle periods, for example over 28 successive 24 hour periods. Preferably the apparatus includes display means for displaying the number of cycle periods for which therapy has been performed. The apparatus may also include means defining a number of the cycle periods for which therapy is to be performed, and display means for indicating during therapy the remaining number of cycle periods to be performed for achieving said defined number. The apparatus may be arranged to switch off automatically when the defined number of cycle periods has been completed, or alternatively, may continue running with the display means indicating that the therapy is completed.

The apparatus according to the invention can conveniently be embodied as a battery driven portable device for attachment to a patient, the device being disposed of when therapy is completed. Completion of therapy may be when a defined number of cycle periods has elapsed or when the battery becomes drained. The device may be activated by a once only action switch as described in European Patent Application No. 83302832.7 and corresponding U.S. Application Ser. No. 495,619.

BRIEF DESCRIPTION OF THE DRAWINGS

The invention will now be described by way of example, with reference to the accompanying drawings in which.

DETAILED DESCRIPTION OF THE PREFERRED EMBODIMENTS

Figure 1:
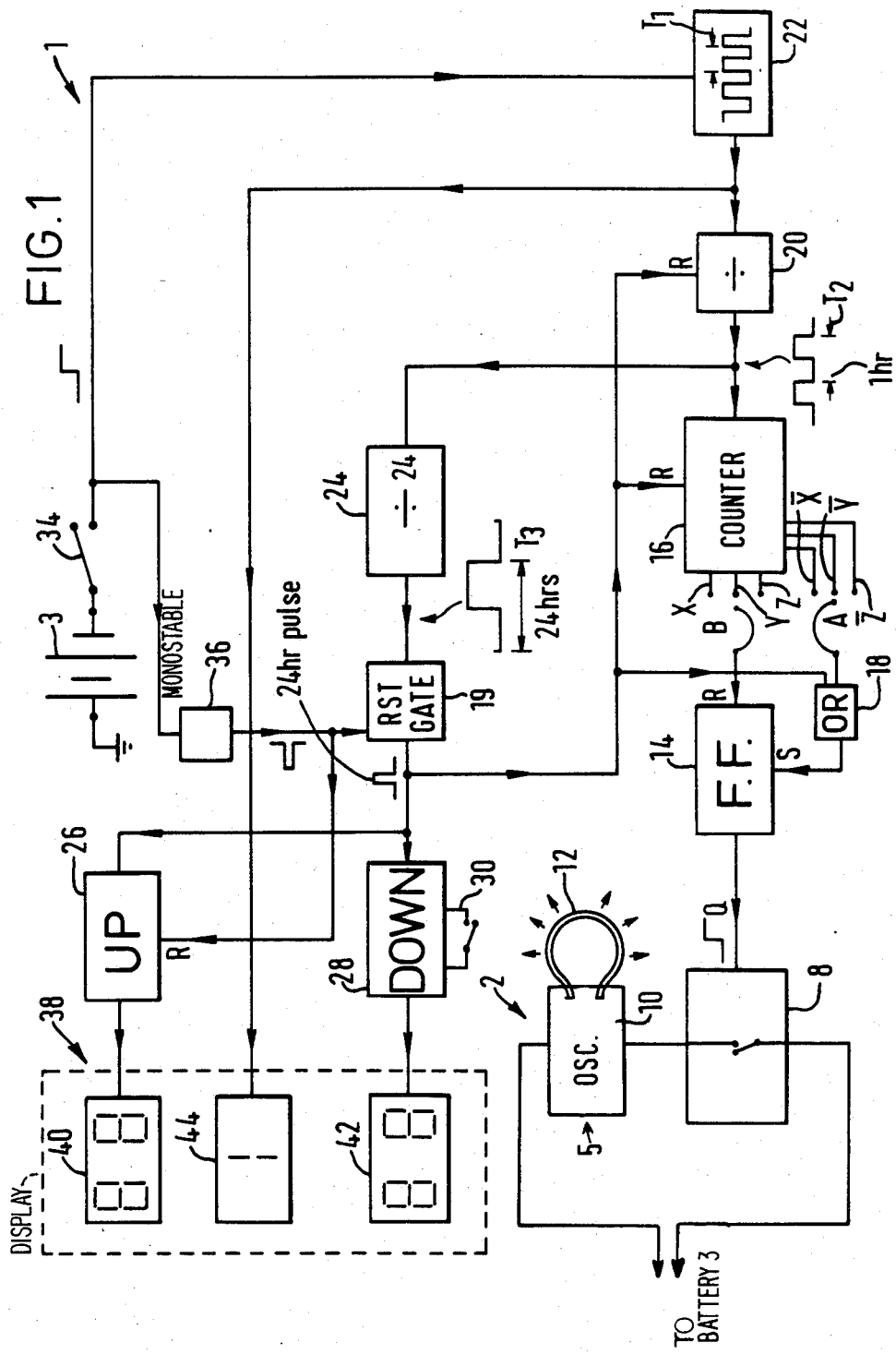
FIG. 1 is a schematic circuit diagram of a therapy apparatus according to the invention.

With reference to FIG. 1 the therapy apparatus comprises a timer circuit 1 connected to a treatment device circuit generally designated 2.

The treatment device circuit 2 includes a battery 3, a treatment device 5 and a single pole single throw (SPST) voltage controlled semiconductor switch 8.

The treatment device 5 includes an oscillator 10, powered by the battery 3 via the switch 8. The oscillator 10 is arranged to cooperate with an antenna 12 to generate and emit a r.f. field for application to a patient to produce therapy of wounded tissue. The antenna may comprise a flexible member for being conformable to the shape of an area of tissue to be treated. The antenna may comprise a loop of coaxial cable. The inductance of the antenna may be utilised as a frequency determining component of the oscillator as described in published British Patent Application No. 2,057,594 or as described in European Patent Application No. 83302832.7.

The r.f. field emitted by the antenna is of such a field strength, that when the antenna is disposed on the patient, no significant tissue heating occurs. The maximum intensity is typically less than 100 $\mu W\ cm^{-2}$ as measured at the skin of the patient. The r.f. field is pulsed and the r.f. pulses are nominally of 100 $\mu sec$ duration, produced once every 1000 $\mu sec$.

The SPST switch is controlled by a signal Q from a set-reset flip-flop 14. The reset input R to flip-flop 14 is connected, via a link B, to a selected output X,Y,Z of a programmable counter 16. The set input S to the flip-flop 14 is connected to an OR gate 18, which performs an OR function on two inputs: the first from a link A, which receives a preselected complimentary input $\overline{X}, \overline{Y}, \overline{Z}$ from the programmable counter 16, and the second input from a reset gate 19.

The reset gate 19 performs a reset function on various parts of the circuitry, to be explained hereinafter.

Figure 2:
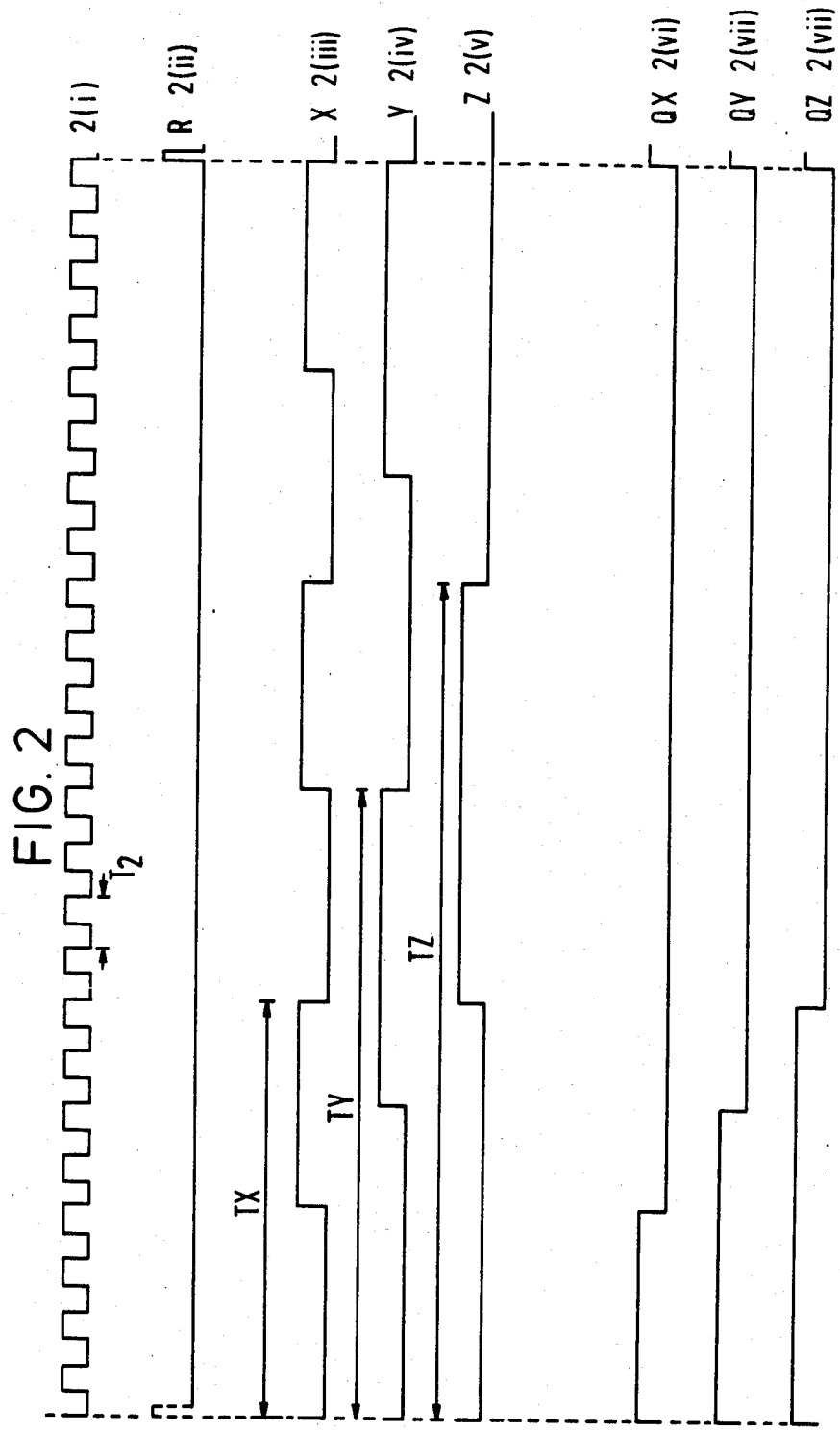
FIG. 2 is a waveform diagram showing output waveforms at various parts of the circuitry shown in FIG. 1.

A square wave clock 22 is connected to the programmable counter 16, via a divider circuit 20. The square wave clock generates a waveform having a predetermined period $T_1$ of 1/2048 hours ($\frac{1}{2}^{11}$). The divider divides the waveform by 2048, to give a waveform of period $T_2$ of one hour, which is fed to the counter 16. This input waveform is shown in FIG. 2, waveform 2 (i).

The waveform 2 (i) is also fed to a further divider circuit 24 which divides the waveform 2 (i) by 24 to give a waveform defining a cycle period $T_3$ of 24 hours. This waveform is fed to the reset gate 19, which generates a pulse FIG. 2, waveform 2 (ii) at the end of each 24 hour period $T_3$. This pulse is fed to the OR gate 18, the counter 16, the divider 20, an up counter 26 and a down counter 28.

The down counter 28 is provided with a push button digital stepper 30, so that a preset number of 24 hour cycle periods can be defined in the counter 28. The preset number is decremented by the output signal from the reset gate 19.

The up counter 26 is incremented from zero by the output signal from the reset gate 19.

The timer 1 is turned on by a power switch 34, which provides power from the battery 3 to the oscillator 22 and also to a monostable 36. The switch 34 may be a once only action switch as described in European Patent Application No. 83302832.7. The monostable 36 produces a reset/refresh pulse to the up counter 26, to set it to zero, and to the reset gate 19.

A display generally designated 38 is connected to the counters 26, 28. A first portion 40 of the display 38 gives a visual indication of the number of elapsed 24 hour periods since the switch 34 was depressed. Similarly, the portion 42 of the display 38 gives a visual indication of the difference between the number of 24 hour periods which have elapsed since switch 34 was operated to actuate the device, and the preset number entered into the down counter 28. A further portion 44 of the display 38 receives the output signal from the oscillator 22 and gives a flashing visual indication that the circuit is functioning. The display 38 is preferably of LCD type.

When the treatment device 5 is to be used on an area of damaged tissue, it is positioned with the antenna 12 overlying the affected area, and the switch 34 is operated. Power fed via the switch 34 turns on the oscillator 22 which starts generating a square wave output waveform having a period $T_1$ as explained earlier. It will readily be appreciated that other components of the circuit will also be powered by the switch 34, although the relevant connections are not shown. The counter 28 may be powered continuously by the battery 3 so as to hold its preset number prior to actuation of switch 34. Alternatively, the counter 28 may include non-volatile storage, so that the power to counter 28 can be connected in response to actuation of switch 34. The output from the switch 34 also triggers the monostable vibrator 36 which resets the up counter to zero as well as initiating the first "24 hour" pulse at t=o from the reset gate 19. This resets the divider circuit 20, the counter circuit 16 and sets the flip-flop 14 which activates the switch 8 and provides power to the oscillator 10 thus generating a r.f. field through the antenna 12. The up and down counters 26, 28 also receive the first reset pulse, but these signals are ignored so that the display 40 shows "00" and the display 42 shows the number of 24 hour periods preset into the down counter 28, until the next pulse is received following the expiration of the first 24 hour period.

Figure 3:
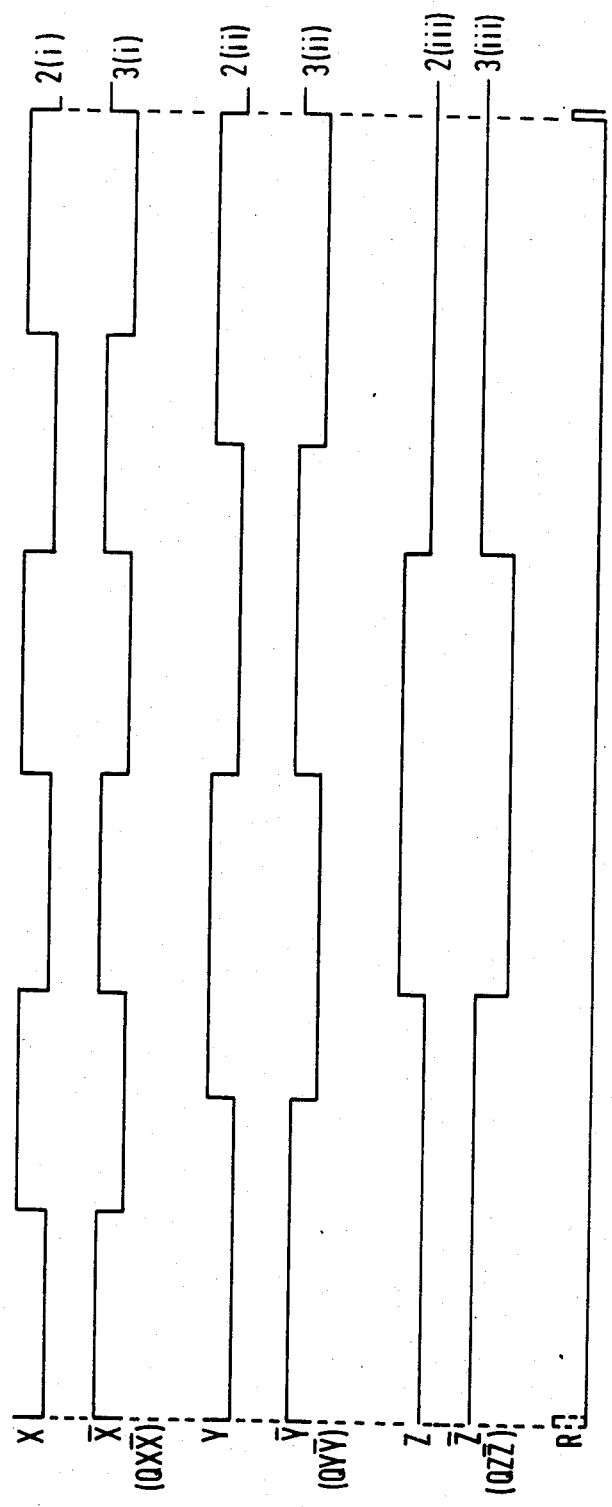
FIG. 3 is a further waveform diagram showing the circuitry of FIG. 1 in an alternative mode of operation.

The square wave signal from the counter 22 is divided by the divider circuit 20 to form the output waveform 2 (i) in FIG. 2 which is fed to the divider 24 and the counter 16 as described earlier. The counter 16 provides further dividing functions to produce output waveforms at terminals X, Y, Z defining portions of different duration of the 24 hour cycle period, as shown in FIG. 2, waveforms 2 (iii), 2 (iv) and 2(v) respectively. In this embodiment these different duration portions have been chosen as eight hours (TX), twelve hours (TY) and sixteen hours (TZ). Complimentary outputs X, Y, and Z are also generated as shown in FIG. 3.

Link B is connected to one of the outputs X,Y, Z. As the flip-flop 14 is reset by a leading edge, it will be reset after four hours if terminal X is selected, after six hours if terminal Y is selected, and after eight hours if terminal Z is selected.

In a first mode of operation of the timer, the link A is not connected to any of the complimentary outputs $\overline{X}$, $\overline{Y}$, $\overline{Z}$ and is connected to ground. This results in the flip-flop 14 generating an output waveform as shown in FIG. 2, waveforms 2 (vi) to 2 (viii), for the X, Y and Z outputs respectively connected to link B. The reset gate generates a pulse every 24 hours to set the flip-flop 14 which is then reset by the first leading edge of the chosen output FIG. 2, waveform 2 (iii), 2 (iv) or 2(v). Twenty four (24) hours later, the reset gate generates a further pulse which resets the counter 16 and sets the flip-flop, so reactuating the switch 8 and commencing the next cycle period.

In an alternative mode of operation, the link A is connected to the output which is complimentary to that of link B. In this case, the flip-flop is set every input period and reset a half period after being set, until the receipt of the 24 hour pulse from the reset gate at which time the cycle is recommenced, as shown in FIG. 3. As can be seen, waveforms 3(*i*) to 3(*iii*) are the compliments of waveforms 2(*i*) to 2(*iii*) respectively.

As mentioned above, the pulses from the reset gate also increment and decrement the up and down counters respectively, so giving a visual indication of the number of 24 hour periods of treatment remaining, as well as the number of periods elapsed.

The switch 30 and links A, B are preferably preset during assembly to desired values and connections.

In the preferred embodiment, the timer and treatment device are designed to be inexpensive to produce and disposable after use.

In the embodiment of FIG. 1 the down counter only indicates the elapsed number of days of treatment and does not perform an on/off function when treatment is complete. In a further embodiment shown in FIG. 4, when the down counter reaches zero days, the treatment circuit is switched off by a switch 48. The inclusion and operation of switch 48 is the principal distinction between the circuits of FIGS. 1 and 4.

Figure 4:
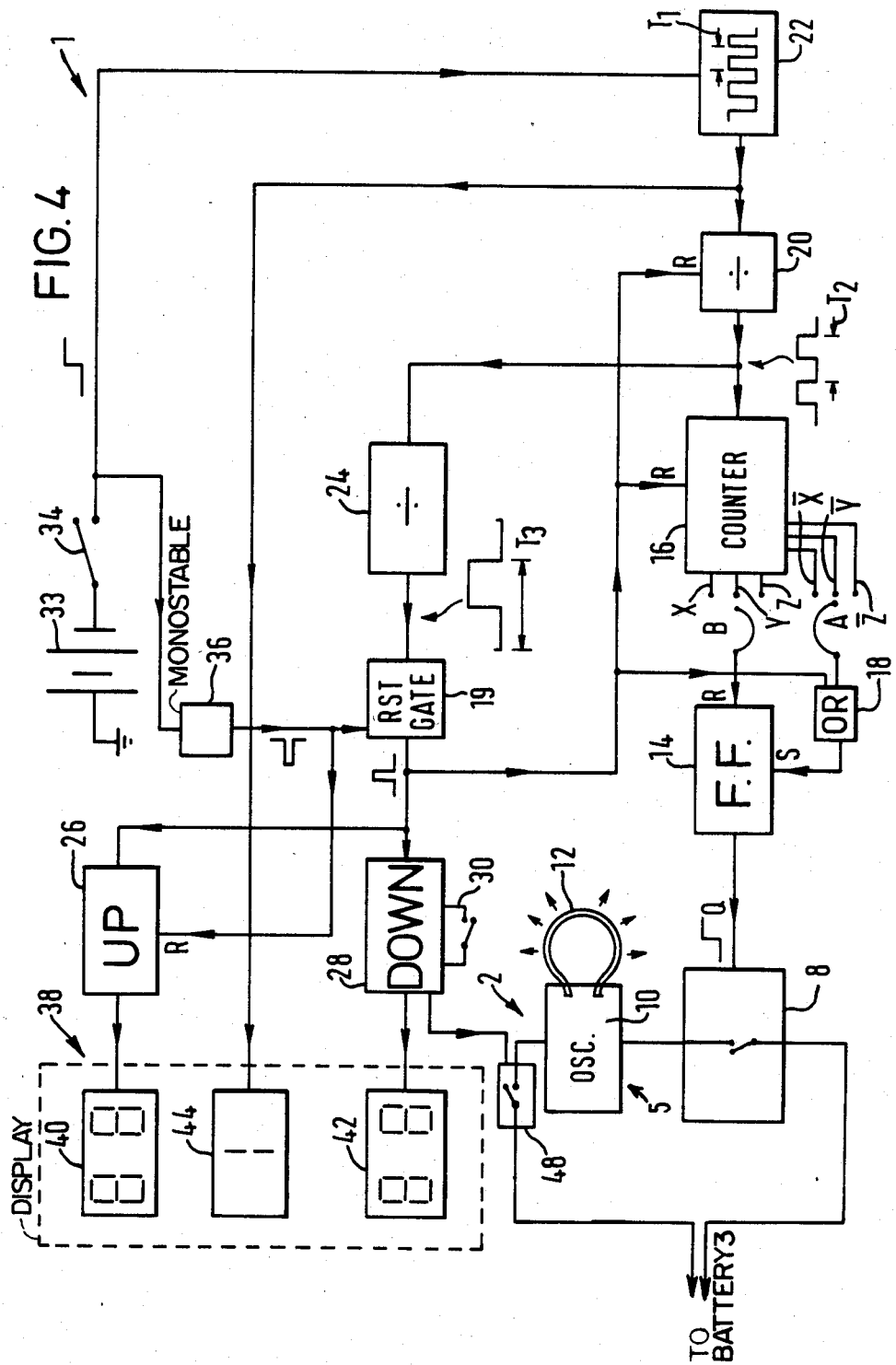
FIG. 4 is a schematic diagram of a second embodiment of the invention.

The device can be constructed as a portable apparatus with the circuit shown in FIGS. 1 or 4 formed in a simple sealed housing, the battery being included in the housing at the time of manufacture of the apparatus. The antenna may protrude from the sealed housing as described in the European application aforesaid.

The timing functions described in relation to FIGS. 1 to 4 can also be performed by means of a microprocessor as will now be described with reference to FIG. 5.

Figure 5:
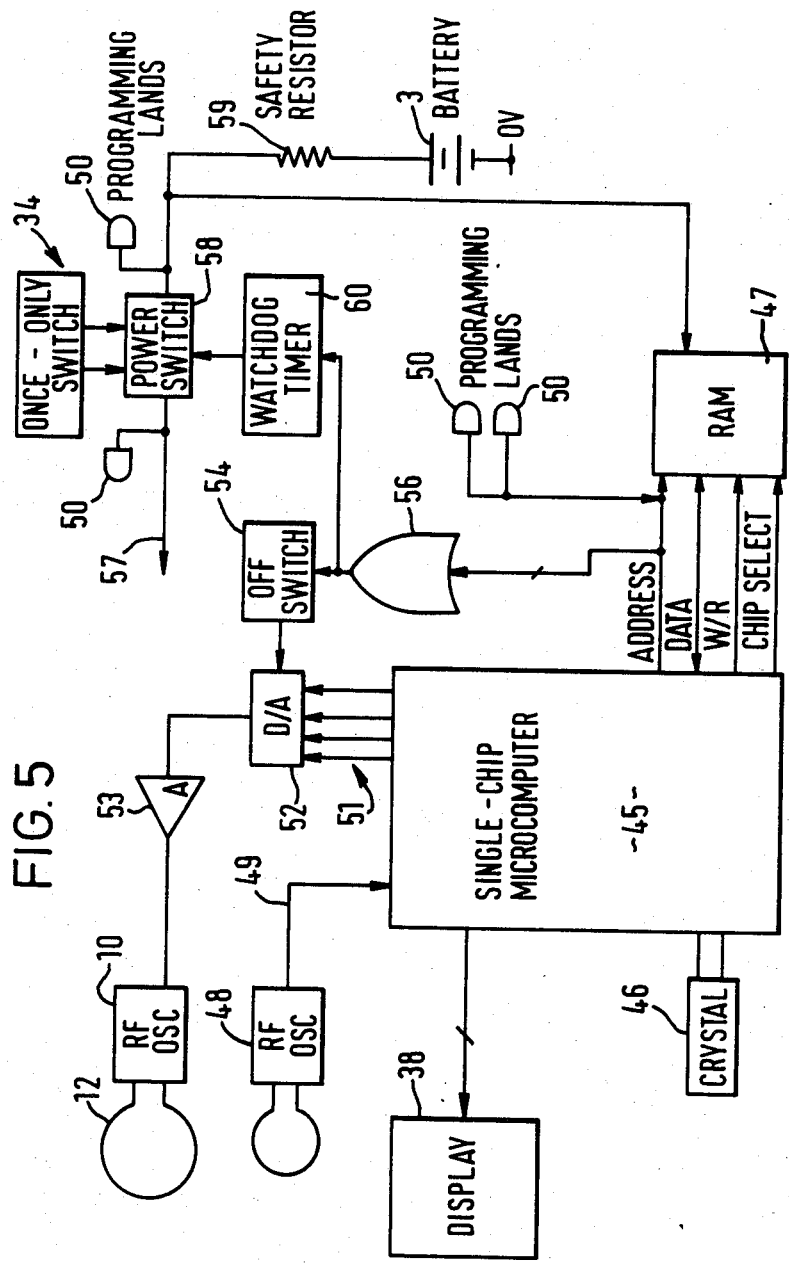
FIG. 5 is a schematic block diagram of an embodiment of the invention utilising a microprocessor.

In FIG. 5, a microprocessor chip 45, driven under the control of a crystal clock oscillator 46, runs programs under the control of program data in a random access memory RAM 47. The microprocessor 45 controls operation of the r.f. oscillator 10 and also drives the display 38. Additionally a r.f. sensor coil and associated detector circuitry 48 are arranged to provide a signal on line 49 indicative that the oscillator is actually delivering the r.f. field. The microprocessor 45 determines if the program is instructing the r.f. oscillator 10 to operate, and instructs the display 38 to indicate an error if the r.f. field is not detected by the circuitry 48.

The arrangement is programmable via programming lands 50 in the circuit, which permit probes to apply programming data streams to the circuit during its manufacture. The use of the microprocessor permits a single circuit design to be programmed for different applications so that different timed treatment patterns may be accomplished.

In particular, the r.f. level produced by the antenna is programmable and the processor 45 produces a 4 bit word on lines 51 indicative of the current programmed level. The digital word is converted to an analog voltage level by a digital to analog converter 52. This analog voltage is fed to an amplifier 53 which controls the level of the r.f. output of the oscillator 10.

The r.f. oscillator is operated to produce a pulsed r.f. field and both the pulse width and pulse repetition rate are programmable. Conveniently, the pulse repetition rate is programmable as follows:

5 Hz steps for 1–200 pulses/second
 10 Hz steps from 200–500 pulses/second
 15 Hz steps from 500–1200 pulses/second The pulse width is conveniently programmable between 10 $\mu S$ to 100 $\mu S$ in 10 $\mu S$ steps.

The treatment pattern is repeated every 24 hours with a minimum time of 15 minutes between changes of parameters. The r.f. oscillator is switched off in the treatment pattern by means of a switch 54. A particular address bit combination for RAM address line 55 is dedicated to operate the switch 54, via a gate 56.

Electrical power for the circuit is supplied on line 57 from the battery 3 under the control of the once only action switch 34. The switch 34 in this embodiment comprises a touch sensitive switch element which operates a latch (not shown). The latch operates a power switch 58, typically comprising a transistor. A safety resistor 59 prevents over-heating in the event of a short-circuit.

A watchdog timer 60 comprising a software driven monostable holds the switch 58 in a conductive condition while sufficient voltage is being supplied from the battery 3 to operate the microprocessor. When the battery voltage falls below this level, the correct operation of the circuit arrangement ceases and the watchdog timer drops out to disconnect the power supply. The battery 3, however, remains connected via line 61 to the RAM 47 to maintain the program data.

It will be appreciated that a plurality of different 24 cycle treatment patterns can be programmed into the circuit arrangement and that the processor 45 can be programmed to change between the patterns as the treatment progresses. If the patterns are kept to a minimum it is possible to dispense with the RAM 47 and utilise solely the storage capacity within the chip 45 for the program data.

Under normal conditions, when the programmed treatment pattern comes to an end, the display 38 shows "End" for 24 hours and then the circuit arrangement shuts down automatically by ceasing to trigger the watchdog timer 60.

In the event of a fault, such as a lack of detected r.f. by the detector circuitry 48, as explained hereinbefore, the display 38 will show "Err" for 24 hours and the circuit arrangement then shuts down automatically by ceasing to trigger the watchdog timer 60.

In the embodiments described hereinbefore, the apparatus has been described for use in treating living tissue to promote healing with an applied r.f. field which does not produce substantial tissue heat-ing. However, the invention has application to applying timed r.f. fields to other living systems. The applied fields may or may not have an athermal effect on the living system. Also, the applied field need not necessarily be used to promote healing but may be used to influence other metabolic processes.

What is claimed is:

1. Electrical apparatus for treating a living system to influence a metabolic growth parameter of the living system, the apparatus comprising:
    field applying means for applying to the system a radio frequency electromagnetic field having a predetermined characteristic and at a power level, measured adjacent a system surface, of not more than approximately 100 $\mu w/cm^2$, for influencing the metabolic growth parameter but without producing bulk heating of the system; and,
    timing means for causing the field applying means to apply said field with said characteristic repetitively, for treatment periods spaced apart in time.

2. Apparatus according to claim 1, wherein said field applying means comprises an r.f. oscillator for producing a pulsed r.f. field; and, the timing means is connected to control the oscillator for intermittent operation defining said spaced apart treatment time periods.

3. Apparatus according to claim 2, wherein the timing means defines a sequence of cycle periods and enables operation of said field applying means for a predetermined portion of each cycle period.

4. Apparatus according to claim 3, further comprising means for selecting the duration of said predetermined portion of the cycle period.

5. Apparatus according to claim 3 further comprising display means for displaying the number of cycle periods for which the apparatus has been operative.

6. Apparatus according to claim 3, further comprising means for defining the number of cycle periods for which the apparatus is to operate; and, display means for indicating the number of cycle periods to be performed for achieving the defined number.

7. Apparatus according to claim 1, wherein said timing means comprises means for storing program instructions to control the duration of said periods.

8. Apparatus according to claim 1, further comprising detector means for detecting operation of said field applying means for verifying operation of the apparatus.

9. Apparatus according to claim 1, further comprising means for selecting the intensity of the electric field produced by the field applying means.

10. Electrical therapy apparatus, comprising:
means for applying a radio frequency electromagnetic field to living tissue at a power level, measured adjacent a tissue surface, of not more than approximately 100 $\mu w/cm^2$, to promote healing thereof but without producing any significant tissue heating; and,
timing means for intermittently applying the field, whereby energy consumption by the field applying means can be substantially reduced without diminution in healing rate.

11. A method for influencing a metabolic growth characteristic of a living system, comprising the steps of:
applying an electric field to a living system at a power level, measured adjacent a system surface, of not more that approximately 100 $\mu w/cm^2$, to alter a metabolic characteristic thereof without thereby heating the living system; and,
periodically interrupting the applying step so that the field is applied repetitively for spaced apart time periods.

12. A method of therapy, comprising the steps of:
applying to living tissue a radio frequency electromagnetic field at a power level, measured adjacent a tissue surface, of not more than approximately 100 $\mu w/cm^2$, to promote tissue healing but without producing any significant tissue heating; and,
periodically interrupting the applying step to apply the field intermittently at a predetermined duty cycle.

* * * * *